US008410048B2

(12) United States Patent
Habermann et al.

(10) Patent No.: US 8,410,048 B2
(45) Date of Patent: Apr. 2, 2013

(54) METHOD FOR PRODUCING INSULIN ANALOGS HAVING A DIBASIC B CHAIN TERMINUS

(75) Inventors: Paul Habermann, Frankfurt am Main (DE); Frank Zocher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 282 days.

(21) Appl. No.: 12/349,854

(22) Filed: Jan. 7, 2009

(65) Prior Publication Data

US 2009/0192073 A1 Jul. 30, 2009

Related U.S. Application Data

(63) Continuation of application No. PCT/EP2007/005933, filed on Jul. 5, 2007.

(30) Foreign Application Priority Data

Jul. 11, 2006 (DE) .......................... 10 2006 031 955

(51) Int. Cl.
*A61K 38/28* (2006.01)
*A61K 38/48* (2006.01)
*C07K 14/62* (2006.01)
*C12N 9/76* (2006.01)

(52) U.S. Cl. ........... 514/5.9; 514/6.2; 514/6.3; 530/303; 424/94.64; 435/213

(58) Field of Classification Search .................. None
See application file for complete search history.

(56) References Cited

U.S. PATENT DOCUMENTS

| 4,320,196 | A | * | 3/1982 | Morihara et al. ............ 435/68.1 |
| 5,015,728 | A | * | 5/1991 | Obermeier et al. ........... 530/303 |
| 5,227,293 | A | | 7/1993 | Stengelin et al. |
| 5,656,722 | A | | 8/1997 | Dorschug et al. |
| 5,663,291 | A | | 9/1997 | Obermeier et al. |
| 6,875,589 | B1 | | 4/2005 | Dorschug et al. |
| 7,091,032 | B2 | * | 8/2006 | Annibali ................ 435/254.23 |

FOREIGN PATENT DOCUMENTS

| EP | 0132769 | 2/1985 |
| EP | 0214826 | 3/1987 |
| EP | 0254516 | 1/1988 |
| EP | 0294851 | 12/1988 |
| EP | 0140084 | 6/1990 |
| EP | 0229998 | 7/1992 |
| EP | 0376156 | 3/1996 |
| WO | WO 01/04156 | 1/2001 |
| WO | WO 02/066628 | 8/2002 |
| WO | WO 02/068660 | 9/2002 |
| WO | WO 02/070722 | 9/2002 |
| WO | WO 03/044210 | 5/2003 |
| WO | WO 03/105888 | 12/2003 |
| WO | WO 2004/005342 | 1/2004 |
| WO | WO 2006/015879 | 2/2006 |
| WO | WO 2006/058620 | 6/2006 |
| WO | WO 2007/036299 | 4/2007 |

OTHER PUBLICATIONS

Dunn et al., Insulin Glargine, Drugs, 63, 1743-1778, 2003.*
Barnett, A., et. al. , Insulin Analogues, The Lancet, vol. 349, pp. 47-51, (1997).
Hartmann, H., et. al., Biological Activity of des-B26-B30)-Insulinamide and Related Analogues in Rat Hepatocyte Cultures, Diabetologia, (1989), vol. 32, pp. 416-420.
Leyer et al, The role of the C-terminus of the insulin B-chain in modulating structural and functional properties of the hormone, International Journal of Peptide & Protein Research, vol. 46, No. 5, Nov. 1995, pp. 397-407.
Sanger, F., et. al., The Amide Groups of Insulin, The Biochemical Journal, (1955) vol. 59, No. 3, pp. 509-518.
Schellenberger et al., Attempts for Quanitfying the S' Subsite Specificity of Serine Proteases, Advances in The Biosciences, Peptides and Proteases: Recent Advances; Selected Papers Presented At the 2nd International Meeting on The Molecular and Cellular Regulation of Enzyme Activity, vol. 65, (1987), pp. 159-166.
Schellenberger et al., Protease-Catalyzed Kinetically Controlled Peptide Synthesis, Angewante Chemie, International Ediition, vol. 30, No. 11, 1991, pp. 1437-1449.
The Effect of Intensive Treatment of Diabetes on the Developement and Progression of Long-Term Complications in Insulin-Dependent Diabetes Mellitus, The New England Journal of Medicine vol. 329, No. 14, pp. 977-986 (1993).

* cited by examiner

*Primary Examiner* — Elly-Gerald Stoica
(74) *Attorney, Agent, or Firm* — Scully, Scott, Murphy & Presser, P.C.

(57) ABSTRACT

The invention relates to a method for producing a type of insulin by genetically engineering a precursor thereof and converting said precursor to the respective insulin in an enzyme-catalyzed ligation reaction with lysine amide or arginine amide, or by lysine or arginine which is modified by protective groups, and optionally subsequent hydrolysis.

21 Claims, No Drawings

METHOD FOR PRODUCING INSULIN ANALOGS HAVING A DIBASIC B CHAIN TERMINUS

This application is a continuation of International application No. PCT/EP2007/005,933, filed Jul. 5, 2007, which is incorporated herein by reference in its entirety; which claims the benefit of priority of German Patent Application No. 10 2006 031 955.9, filed Jul. 11, 2006.

DESCRIPTION

The invention relates to a method for preparing an insulin with dibasic chain end by biotechnological preparation of a precursor thereof and subsequent conversion in an enzyme-catalyzed ligation reaction with lysinamide or argininamide, or lysine or arginine modified by protective groups, and optionally subsequent hydrolysis, to give this insulin.

About 177 million people around the world suffer from diabetes mellitus. These include about 17 million type I diabetics for whom replacement of the lacking endocrine insulin secretion is the only possible therapy at present. Those affected are dependent on insulin injections, usually several times a day, throughout life. Type II diabetes contrasts with type I diabetes in that there is not always a deficiency of insulin, but in a large number of cases, especially in the advanced stage, treatment with insulin, where appropriate combined with an oral antidiabetic, is regarded as the most favorable type of therapy.

In healthy people, insulin release is strictly coupled to the blood glucose concentration. Elevated blood glucose levels like those occurring after meals are rapidly compensated by a corresponding rise in insulin secretion. In the fasting state, the plasma insulin level falls to a baseline value which suffices to ensure a continuous supply of glucose to insulin-sensitive organs and tissues and to keep hepatic glucose production low during the night. Replacement of the endogenous insulin secretion by exogenous, usually subcutaneous administration of insulin usually does not come close to the quality of the physiological regulation of blood glucose described above. Upward or downward rearrangements of the blood glucose level are frequent and may, in their most severe forms, be life-threatening. However, in addition, elevated blood glucose levels lasting for years represent, even without initial symptoms, a considerable health risk. The large-scale DCCT study in the USA (The Diabetes Control and Complications Trial Research Group (1993) N. Engl. J. Med. 329, 977-986) unambiguously proved that chronically elevated blood glucose levels are substantially responsible for the development of late diabetic complications. Late diabetic complications and micro- and macrovascular damage which in some circumstances becomes manifest as retinopathy, nephropathy or neuropathy and leads to blindness, renal failure and loss of extremities and, in addition, is associated with an increased risk of cardiovascular disorders. It is to be inferred therefrom that an improved therapy of diabetes must primarily aim at keeping blood glucose as closely as possible within the physiological range. The intensive insulin therapy policy intends to achieve this by injections several times a day of fast- and slow-acting insulin preparations. Fast-acting formulations are given at meal times in order to compensate the postprandial rise in blood glucose. Slow-acting basal insulins are intended to ensure the basic supply of insulin especially during the night without leading to hypoglycemia.

Insulin is a polypeptide composed of 51 amino acids divided into 2 amino acid chains: the A chain with 21 amino acids and the B chain with 30 amino acids. The chains are linked together by 2 disulfide bridges. Insulin preparations have been employed for many years for the therapy of diabetes. Moreover, not only are naturally occurring insulins used, but more recently also insulin derivatives and analogs.

Insulin analogs are analogs of naturally occurring insulins, namely human insulin or animal insulins which differ by replacement of at least one naturally occurring amino acid residue by other amino acid residues and/or addition/deletion of at least one amino acid residue from the corresponding, otherwise identical, naturally occurring insulin. U.S. Pat. No. 5,656,722 for example describes des-Phe$^{(B1)}$-insulin derivatives. The amino acid residues which have been added and/or replaced may also be ones which do not occur naturally.

Insulin derivatives are derivatives of naturally occurring insulins or insulin analogs in which one or more amino acid residues and/or the N or C termini of the A and/or B chain are replaced by functional groups. The functional groups are selected from a group comprising amide residues, amine residues, carboxyl residues, alkyl residues, alcohol residues and alkoxy residues.

An efficient insulin therapy makes use of so-called basal insulins. By these are meant formulations which make slow, continuous release of exogenously administered insulin possible. In this way, a baseline insulin concentration in the body which has advantageous effects on the physiological condition of the person suffering from diabetes is achieved over a lengthy period.

The recombinant insulin analog Gly(A21), Arg(B31), Arg(B32) human insulin (insulin glargine) is in this connection notable for needing to be supplied to the body only every 24 hours—i.e. only one a day—in order to achieve a basal effect. The once-a-day administration leads to an improved quality of life. The improved physiology leads for example to a reduction in the Hba1c level and it can be expected that, owing to this improvement, the late sequelae of diabetes will appear—if at all—considerably later, thus making it possible to prolong the life expectancy of the relevant diabetic.

The demand for this insulin analog is correspondingly high. Since the number of diabetics is continually increasing, it is moreover of economic interest to minimize the costs for preparing corresponding analogs. U.S. Pat. No. 5,656,722 describes the possible preparation of insulin analogs via a preproinsulin fusion protein which consists of a fusion portion ("pre portion") and of a monkey proinsulin variant. One of the analogs described comprises glycine instead of asparagine in position A(21). The corresponding fusion protein is a peptide precursor variant for preparing insulin glargine. The method provides for deletion of the pre portion and the C peptide from this fusion protein by reaction with trypsin. EP-A 0 668 292 describes a fusion protein which follows the same principle but allows insulin glargine to be prepared by a method which is an improvement over U.S. Pat. No. 5,656,722. It is clear to the skilled worker in this connection that a partial cleavage is possible in particular at the boundary of the insulin B chain and C chain, which is defined by the dibasic structure Arg-Arg, and leads to a B31 mono-arg human insulin analog. This faulty product must be removed from the actual compound of interest. This leads to a marked impairment of the yield. The problem can be avoided by recombinant preparation of proinsulins and reaction thereof with a specific endoprotease such as, for example, lysyl endopeptidase, and reacting the resulting des-B30 human insulin (analog) in a semisynthetic peptide chemistry approach with the tripeptide Thr-Arg-Arg. EP-A 0 132 769 and WO 2003/044210 describe the need to protect the reactive groups of the tripeptide during the reaction. The protective groups are eliminated subsequent to the reaction. This route is associated with costs arising from the preparation of the tripeptide by chemical synthesis and the introduction of protective groups.

Thus, it would be desirable to have a method allowing Arg (B31), Arg(B32)-insulin analogs to be prepared from the Arg(B31) human insulin precursor.

German patent application No. 10 2005 046 113.1 (not published) describes a method including the trypsin-catalyzed ligation of amino acids which have C-terminal amidation to peptides whose C-terminal amino acid consists of lysine or arginine. The yields observed in this case are surprisingly high and it is moreover possible to carry out the coupling reaction without masking with protective groups. The reaction takes place in a nonaqueous medium. It has now surprisingly been found that the coupling of arginine amide or lysine amide to B31 insulin analogs is possible with high yields. It is moreover surprisingly to control the reaction so that there is preferential formation of insulin analogs of the form Arg(B31), Arg(B32)-human insulin amide or of the form Arg(B31), Lys(B32)-human insulin amide. The yield is moreover greater than 60%. The amide group can be eliminated by acidic hydrolysis at the end of the reaction. It has likewise been surprisingly found that it is possible as alternative to lysinamide or argininamide to employ in the reaction arginine or lysine possibly having a protective group. Protective groups which may be mentioned as example are t-butyloxycarbonyl (Boc) or dimethoxyphenylpropyloxycarbonyl (DZZ). Since there are descriptions in the literature that in particular protected arginine derivatives may be unstable in various solvents, it is clear to the skilled worker that there is continuous development of new protective groups which have the effect of improved stability in peptide chemistry. A positive influence on the yield is possible by varying the reaction conditions according to the protective groups or amide group. This is familiar to the skilled worker and the invention also relates thereto. The partial cleavage product B(31) human insulin, which in the preparation of insulin glargine or comparable Arg(B31), Arg(B32)-insulin analogs from preproinsulin precursors (U.S. Pat. No. 5,656,722) thus becomes available for preparing the product of value. Corresponding fusion proteins need not in this case be prepared intracellularly. It is clear to the skilled worker that proinsulin analogs can also be prepared by bacterial expression with subsequent secretion into the periplasm and/or into the culture supernatant. European patent application EP-A 1 364 029 describes this by way of example. The invention also relates to the use of Arg(B31)-human insulin precursors resulting directly after expression from such bacterial methods.

There is in addition a further technical aspect of the method, to which the invention likewise relates. European patent application EP-A 0 347 781, and European patent applications EP-A 1 364 030 and EP-A 1 364 032, describe yeast-based methods for preparing miniproinsulins with high yields. Extension of such a method or a similar one to the preparation of miniproinsulins which have the amino acid residues described in U.S. Pat. No. 5,656,722, i.e. Gly, Ala, Val, Leu, Ile, Pro, Phe, Trp, Met, Ser, Thr, Cys, Tyr, Asp or Glu, in position A21 allows these miniproinsulins to be converted into the Arg(B31), Arg(B32)-insulin analogs immediately after cleavage into the two-chain insulin.

If the expression takes place, as described in EP-A 1 364 032, via a fusion protein, it is advantageous not to eliminate the pre portion with trypsin or similar endoproteases. Instead, a cleavage site which is recognized by a specific endoprotease which does not cleave the insulin derivative is incorporated in order to eliminate the pre or fusion portion appropriately. Enterokinase (DDDDK) or factor Xa (IEGR) are mentioned by way of example. The invention also relates thereto. It is moreover clear to the skilled worker that the two cleavage reactions can proceed in a one-pot reaction. A further possibility is to eliminate the fusion portion only in a following step. The fusion protein portion can in this case be chosen to be derivatives of a large number of efficiently secreted proteins. Examples which may be mentioned for bacteria are DHFR (dihydrofolate reductase), glutathione S-transferase and hirudin. Examples which can be used for yeast secretion are albumin or derivatives thereof, superoxide dismutase or derivatives, interleukin 2 or derivatives and hirudin or derivatives. In the present application, by way of example a hirudin derivative is used as fusion portion both for bacterial expression and for yeast expression. It has in this connection surprisingly been found that the hirudin sequence can be further modified by introducing a peptide sequence of consecutive histidines and/or a peptide sequence DDDDK which represents the recognition site for enterokinase, without adversely affecting the folding of the miniproinsulin portion. Methods of affinity chromatography are thus made available. The invention also relates thereto.

The skilled worker is further familiar with the fact that the expression systems described by way of example represent only a small segment of the host/vector systems developed for the recombinant preparation of proteins. Host/vector systems permitting the preparation of the target peptides thus also form part of the invention.

The invention thus relates to the preparation of insulin analogs which are characterized by the presence of the amino acid residues Arg(B31), Arg(B32) or Arg(B31), Lys(B32) from Arg(B31)-human insulin precursors of the analogs via trypsin-catalyzed ligation with arginine or lysine. It is clear to the skilled worker in this connection that, because of the surprising selectivity of the reaction, the ligation reaction can also be repeated over a plurality of reaction cycles, so that insulin analogs having further basic amino acids lysine or arginine beyond positions B31 and B32 become available. This is achieved by carrying out a coupling reaction, deamidating or deprotecting the terminal amino acid, and employing the product anew in an appropriate following reaction cycle. Such products can likewise be obtained by using an analog already having Arg(B31), Arg(B32) or Arg(B31), Lys (B32) as precursor. It is likewise possible to prepare analogs which comprise in position B31 and thereafter any genetically encodable amino acids which need not be arginine or lysine in sequence, but whose C-terminal end is characterized by the dibasic sequence Arg-Arg, Arg-Lys, Lys-Lys or Lys-Arg. The reaction is moreover not limited to the use of trypsin as catalyst. It is familiar to the skilled worker that, besides the known commercially available rat, bovine, porcine or human trypsins or other isoenzymes or derivatives or variants thereof, it is also possible to use the following enzymes: cathepsin, trypsin from *Fusarium oxysporum* and from *Streptomyces* (*S. griseus*, *S. exfoliatus*, *S. erythraeus*, *S. fradiae* and *S. albidoflavus*), tryptase, mastin, acrosin, kallikrein, hepsin, prostasin I, lysyl endopeptidase (Lysin-C) and endoproteinase Arg-C (clostripain).

The invention therefore relates to a method for preparing an insulin analog or a derivative thereof, in which a naturally occurring, basic amino acid which is amidated or protected C-terminally with a protective group, or a peptide which consists of naturally occurring, basic amino acids or analogs or derivatives thereof and is C-terminally amidated or protected with a protective group, is added onto an initial insulin analog or a derivative thereof whose C-terminal amino acid of the A and/or B chain is selected from a group comprising naturally occurring, basic amino acids or analogs or derivatives thereof, onto one of said C-terminal amino acids in the presence of an enzyme having the biological activity of trypsin, and the resulting modified insulin analog is purified and optionally the amide group or C-terminal protective group of the added amino acid or of the added peptide is eliminated.

The invention further relates to a method as described above, where the insulin analog is characterized by the general formula I

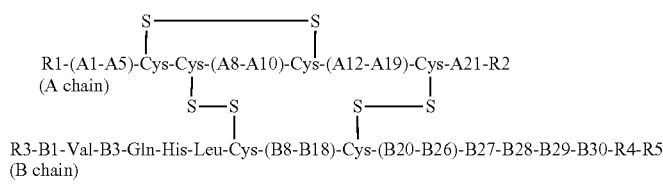

(I)

in which the meanings are
(A1-A5) the amino acid residues in positions A1 to A5 of the A chain of human insulin or animal insulin,
(A12-A19) the amino acid residues in positions A12 to A19 of the A chain of human insulin or animal insulin,
A21 a naturally occurring amino acid residue,
(B8-B18) the amino acid residues in positions B8 to B18 of the B chain of human insulin or animal insulin,
(B20-B26) the amino acid residues in positions B20 to B26 of the B chain of human insulin or animal insulin,
(A8-A10) the amino acid residues in positions A8 to A10 of the A chain of human insulin or animal insulin,
B30 a chemical bond or a naturally occurring amino acid residue,
B1 a chemical bond or a naturally occurring amino acid residue,
B3 a naturally occurring amino acid residue,
B27, B28 and B29 a naturally occurring amino acid residue,
R1 an amino group or one to three naturally occurring amino acid residues,
R2 a carboxy group or one to three naturally occurring amino acid residues,
R3 an amino group or one to three naturally occurring amino acid residues,
R4 a chemical bond or one to three naturally occurring amino acid residues, where the C-terminally occurring amino acid residue represents a basic amino acid,
R5 one or two basic amino acid residues whose C terminus is either free or amidated,
where the amino acid residue whose C terminus is connected to the N terminus of R5 is selected from a group comprising naturally occurring, basic amino acids.

The invention further relates to a method as described above, where the initial insulin analog is characterized by the general formula II where R1, (A1-A5), (A8-A10), (A12-A19), A21, R2, R3, B1, B3, (B8-B18), (B20-B26), B27, B28, B29, B30 and R4 are defined as in claim 1, and the C-terminal amino acid residue of the B chain is selected from a group comprising naturally occurring, basic amino acids.

The invention further relates to a method as described above, where the naturally occurring, basic amino acid which is amidated or protected C-terminally with a protective group is C-terminally amidated arginine or arginine protected C-terminally with a Boc protective group.

The invention further relates to a method as described above, where the modified insulin analog is Gly(A21), Arg(B31), Arg(B32) human insulin whose C-terminal end of the B chain is amidated, with the initial insulin analog being in particular Gly(A21), Arg(B31) human insulin.

The invention further relates to a method as described above, where the initial insulin analog is prepared by recombinant expression of a precursor protein comprising the A chain and the B chain of the initial insulin analog, in particular a method of this type where a gene which is part of a replicon is expressed.

The invention further relates to a method as described above, where a bacterium or a yeast is used as host cell.

The invention further relates to a method as described above, where the precursor protein is secreted after expression, in particular where the precursor protein is isolated from the cellular supernatant of bacteria or yeasts.

The invention further relates to a method as described above, where the precursor protein is isolated from the periplasm of a bacterium.

The invention further relates to a method as described above, where the precursor protein obtained as claimed in any of said claims is subjected to a folding process and enzymatic cleavage.

The invention further relates to a method as described above, where the initial insulin analog is prepared by recombinant direct expression.

The invention further relates to a method as described above, where the enzyme having the biological activity of trypsin is selected from a group comprising human trypsin, porcine trypsin, bovine trypsin and a variant of human trypsin, porcine trypsin and bovine trypsin.

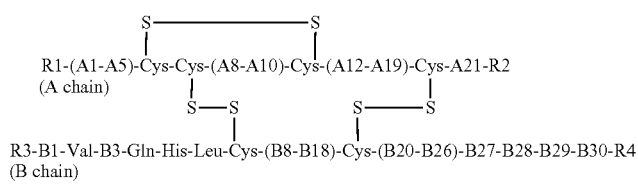

(II)

The invention further relates to a method as described above, where the C-terminal end of the B chain of the modified insulin analog is subsequently deprotected in a hydrolysis reaction.

The invention further relates to a method as described above, in which the resulting insulin analog is Gly(A21), Arg(B31), Arg(B32) human insulin.

The invention further relates to the use of an insulin analog or of a derivative thereof whose C-terminal amino acid of the A and/or B chain is amidated as medicament.

The invention further relates to insulin analog or a derivative thereof obtainable by a method as described above, whose C-terminal amino acid of the A and/or B chain is amidated.

The invention is explained in more detail below by means of some procedural examples. These procedural examples are not intended to have a restrictive effect.

EXAMPLE 1

Preparation of Arg(B31), Gly(A21) Insulin from a Fusion Protein after In Vitro Folding U.S. Pat. No. 5,663,291 describes in example 1 therein the obtaining of a correctly folded insulin fusion protein of the structure:

```
                                      (SEQ ID NO.: 1)
MATTSTGNSA RFVNQHLCGS HLVEALYLVC GERGFFYTPK

TRREAEDPQV GQVELGGGPG AGSLQPLALE GSLQKRGIVE

QCCTSICSLY QLENYCG
```

This material is converted in accordance with example 4 of U.S. Pat. No. 5,227,293 by reaction with trypsin into two-chain insulin, and Arg(B31), Arg(B32), Gly(A21) insulin and Arg(B31), Gly)A21) insulin are isolated.

It is thus possible to obtain the Arg(B31), Arg(B32), Gly (A21)-insulin analog directly, while the Arg(B31), Gly(A21) byproduct can be employed as precursor in the trypsin-catalyzed ligation with modified arginine or lysine.

EXAMPLE 2

Preparation of Arg(B31), Gly(A21) Insulin from a Fusion Protein which has been Obtained by Secretion and Comprises Proinsulin Correctly Folded As alternative to example 1, fusion proteins can also be prepared by secretion in bacterial systems. In this case, the proinsulin structure as part of the fusion protein is correctly folded, and the 'in vitro' refolding step can be dispensed with. The patent application WO 02/068660 proposes a system of this type. If, for example, the codon for Asn(A21) is replaced by a codon for Gly(A21) in the plasmid pBpfuHir_Ins which is described in example 1 of this international patent application, the result is a fusion protein from which insulin glargine can be obtained by way of example, and moreover Arg(B31), Gly(A21) human insulin can be isolated as byproduct, as described in example 1.

To prepare the sequence, a new primer insu_a21_gly_rev having the following structure:

```
                                      (SEQ ID NO.: 2)
5'-TTTTTTAAGCTTGTCGACTCATTAGCC GCAGTAGTTCTCCAGCTG-
3'
``` is required.

This primer is employed in analogy to the patent application WO 02/068660 with the primer pfu1 on DNA of the plasmid pBpfuHir_ins in a PCR. It is possible to isolate from the PCR product a BamH1/Hind3 fragment that can be cloned in accordance with the example of the patent application WO 02/068660. After expression, a fusion protein is isolated and is treated further in accordance with example 1 of the present application.

It is clear to the skilled worker that the precursor Arg(B31), Gly(A21) human insulin can also be obtained directly by bacterial secretion of a fusion protein. The invention also relates thereto.

EXAMPLE 3

Preparation of Arg(B31), Arg(B32), Gly(A21)-Insulin from an Arg(B31), Gly(A21)-Precursor by Coupling with Argininamide 100 mg of 21A-Gly-30B a L-Arg-insulin are dissolved in 0.95 ml of argininamide solution (446 g/L), and 0.13 ml of M Na acetate buffer (pH 5.8) and 2 ml of DMF are added. The reaction mixture is cooled to 12° C. and started by adding 0.094 ml of trypsin (0.075 mg, Roche Diagnostics).

After 8 h, the reaction is stopped by adding TFA to pH 2.5 and analyzed by HPLC. >60%-Arg(B31), Arg(B32), Gly (A21) human insulin is formed. Addition of trypsin inhibitor solution is followed by purification of the amidated analog in analogy to U.S. Pat. No. 5,656,722. The amidated insulin analog is then hydrolyzed in the presence of acid for several hours to give Arg(B31), Arg (B32), -Gly(A21) human insulin.

EXAMPLE 4

Preparation of Arg(B31), Lys(B32), Gly(A21) Human Insulin from an Arg(B31), Gly(A21) Human Insulin Precursor by Coupling with Lysinamide 100 mg of 21A-Gly-30B a L-Arg-insulin are dissolved in 0.93 ml of lysinamide solution (400 g/L), and 0.13 mL of M Na acetate buffer (pH 5.8) and 2 ml of DMF are added. The reaction mixture is cooled to 12° C. and started by adding 0.094 ml of trypsin (0.075 mg, Roche Diagnostics).

After 8 h, the reaction is stopped by adding TFA to pH 2.5 and analyzed by HPLC. Arg(B31), Lys(B32)-$NH_2$, Gly(A21) human insulin is formed and is purified after addition of trypsin inhibitor solution in analogy to U.S. Pat. No. 5,656, 722. The amidated insulin analog is then hydrolyzed in the presence of acid for several hours to give Arg(B31), Lys (B32), Gly(A21) human insulin.

EXAMPLE 5

Preparation of Arg(B31), Arg(B32), Gly(A21)-Insulin from an Arg(B31), Gly(A21) Precursor by Coupling with H-Arg (Boc)2-OH 0.25 mg of Arg(B31), Gly(A21) human insulin is mixed in an Eppendorf vessel with 11 µl of 0.1 M pyridine acetate buffer (pH 5.6), 60 µl of a 130 g/L solution of H-Arg(Boc)2-OH×HCl in 0.1 M pyridine acetate buffer (pH 5.6) and 119 µl of DMF and incubated with trypsin (Roche Diagnostics) at 12° C. for some hours.

The reaction is stopped by adding a mixture of 25% water, 25% acetonitrile and 50% trifluoroacetic acid. The mixture is lyophilized and, to eliminate the protective group, dissolved in 1 ml of TFA and left to stand at room temperature for about 3 hours. Purification of the Arg(B31), Arg(B32)-NH$_2$, Gly (A21) human insulin takes place by way of example in analogy to U.S. Pat. No. 5,656,722.

EXAMPLE 6

Preparation of Arg(B31), Lys(B32), Gly(A21) Insulin from an Arg(B31), Gly(A21) Precursor by Coupling with H-Lys (Boc)-OtBu 50 mg of Arg(B31), -Gly(A21) human insulin are dissolved in 0.62 ml of H-Lys (Boc)-OtBu solution (0.5 g/mL, pH 5), and 1 ml of N,N-dimethylformamide (DMF) is added. The mixture is cooled to 12° C., and 2 mg of trypsin (Roche Diagnostics) are added.

After more than 10 hours, the reaction is stopped by adding 2 ml of a 50% strength acetonitrile/water mixture and 1 ml of TFA (100%). The mixture is lyophilized and, to eliminate the Boc protective group, dissolved in 1 ml of TFA and left to stand at room temperature for about 3 hours. Purification of the Arg(B31), Lys(B32), OH takes place by way of example in analogy to U.S. Pat. No. 5,656,722.

EXAMPLE 7

Gene Sequence for Secretion of a Hirudin Arg(B31), Gly(A21) Insulin Fusion Protein by Baker's Yeast The patent application EP-A 1 364 032 proposes the use of hirudin as fusion partner for the expression and secretion of other pharmaceutically interesting proteins of value in yeasts.

Example 1 of the patent application EP-A 1 364 032 describes the host-vector system for preparing a fusion protein which consists of a hirudin derivative and miniproinsulin. This system can be used by way of example for preparing miniproinsulins which in position A21 the amino acid asparagine by amino acids as described in U.S. Pat. No. 5,656,722.

The expression vector can be constructed in analogy to the example of the patent application EP-A 1 364 032 if the primer insnco1rev is replaced and designed so that the codon in position A21 is altered.

To prepare the sequence coding for Arg(B31), Gly A(21) human insulin, for example the following primer is synthesized:

```
ins_gly_a21_rev
5'-TTTTTTCCATGGGTCGACTATCAGCCACAGTAGTTTTCCAGCTGG-3'   (SEQ ID NO.: 3)
```

The primer in this case completely covers the gene segment coding for amino acids A15-A21 of the insulin analog. Combination of this primer with the primer of SEQ ID NO:4 from example 1 of the application, and use of the plasmid pADH2Hir_ins as template allows the generation by PCR of a DNA fragment that, after digestion with the restriction enzymes KpnI and NcoI, is inserted into the correspondingly opened expression vector and comprises the desired fusion protein.

The vector is designated pADH2Hir_ins_glyA21. The fusion protein is expressed and processed in accordance with the patent application EP-A 1 364 032 to give Gly(A21)-miniproinsulin, which is converted in accordance with example 2 into Arg(B31), Lys(B32), Gly(A21) human insulin.

EXAMPLE 8

Gene Sequence for Direct Secretion of the Arg(B31), Gly(A21) Precursor by Baker's Yeast DNA of the plasmid pADH2Hir_ins_glyA21 described in example 7 is used to prepare a vector construct for direct secretion of Arg(B31), Gly A(21) human insulin.

The following primers are synthesized.

```
alpha_insf1
5'-TTTTTTGGATCCTTTGGAATAAAAGATTTGTTAACCAACACTTGTGTG-3'   (SEQ ID NO.: 4)
```

It covers the sequence of the C terminus of the alpha-factor, codons for Lys-Arg and of the N-terminus of the miniproinsulin sequence.

```
ins_glyrev2
                                         (SEQ ID NO.: 5)
5'-TTTTTTCCAT GGGTCGCTAT CAGCCACAGT AGTTTTCCAG
CTGG-3'
```

The primer hybridizes with the 3' end of the insulin analog sequence cloned into the plasmid pADH2Hir_ins_glyA21. A PCR (standard conditions) generates a DNA fragment which, after digestion with the restriction enzymes KpnI and NcoI, is inserted into the correspondingly opened expression vector and comprises the desired fusion protein. The in competent cells of the yeast strain Y79 transforms. Transformants are subsequently expressed as described in example 7. The Arg (B31), Gly(A21)-miniproinsulin is isolated by known methods (EP-A 0 229 998) and converted as in example 2 into Arg(B31), Lys(B32), Gly(A21) human insulin.

EXAMPLE 9

Gene Sequence for Secretion of a Hirudin-Arg(B31), Gly(A21) Human Insulin Fusion Protein by *Pichia pastoris*

Cloning of the expression vector takes place in analogy to example 4 of the patent application EP-A 1 364 032. Instead of the sequence primer pichia_H_Irev2, in this case the primer ins_gly_rev2 is employed and later enables the possibility of expression of Gly(A21) human insulin with the PCR product:

5'-TTTTTGGCGCCGAATTCACTACTATTAGCCACAGTAGTTTTCCAGCTGG-3' (SEQ ID NO.:6)

The resulting plasmid is designated pPich_Hir_ins-GlyA21. Purification of Arg(B31), Gly(A21)-miniproinsulin as starting material for generating an analog with dibasic chain end is carried out as described.

EXAMPLE 10

Gene Sequence for Direct Secretion of the Arg(B31), Gly(A21) Precursor by *Pichia pastoris*

The appropriate expression vector is constructed in analogy to example 7. The DNA of the plasmid pPich_Hir_ins-GlyA21 and two primers pich_insgly_dirf and pich_insgly__dirrev pich_insgly_dirf
(SEQ ID NO.:7)
5'-TTTTTCTCGAGAAAAGATTTGTTAACCAACACTTGTGTG-3' pich_insgly_dirrev
5'-TTTTTT GGCGCCGAATTCACTACTATTAGCCAC-3'
(SEQ ID NO.: 8)
are required.

EXAMPLE 11

Preparation of Arg(B31), Gly(A21)-Insulin from a Fusion Protein which is Obtained by Yeast Secretion and Comprises Proinsulin Correctly Folded, and its Fusion Portion Comprises a His$_6$ Amino Acid Sequence DNA of the plasmid pADH2Hir_ins_glyA21 serves as template. Two primers are synthesized:
alpha_LT_H6_hirf and alpha_LT_H6_hirrev alpha_LT_H6_hirf1:
(SEQ ID NO.: 9)
5'-GCACCATCATCACCATCACTATACTGACTGCACTGAATC-3'

The primer comprises the codons for 6 histidines in series and amino acids 3-8 and 9 (partially) of the Refludan® sequence.

alpha_LT_H6_hirf2:
5'-GAAGGGGTACCTTTGGATAAAAGACTTACGCACCATCATCACCATCAC-3' (SEQ ID NO.: 10)

The primer comprises the codons for 6 histidines in series, the codons for amino acids 1 and 2 of the lepirudin sequence and alpha-factor sequences which include the Lys-Arg processing site, and cover the recognition site for the restriction enzyme Kpn 1. DNA of the plasmid pADH2Hir_ins_glyA21 serves as template in a standard PCR with the primers alpha_LT_H6_hirf1 and ins_gly_a21_rev from example 7 of the present application. The product of the reaction is isolated and an aliquot is employed as template for a second PCR with the primers alpha_LT_H6_hirf2 and ins_gly_a21rev. The reaction product is processed as described with KPN1 and Nco1 and then cloned. The result is the plasmid pADH2_LT_H6_Hir_ins_glyA21: following transformation of Y79 with DNA of the plasmid, the fusion protein is expressed. The cells are separated from the supernatant by centrifugation, and the supernatant is concentrated through membrane filters, e.g. from Sartorius, and then by Ni$^{2+}$ affinity chromatography, following the protocol for the Invitrogen ProBond™ purification system. After removal of the elution buffer by dialysis and/or filtration or gel filtration as alternative, the fusion protein can be processed in a known manner to give Arg (B31), Gly (A21) human insulin and then converted into insulin glargine.

EXAMPLE 12

Preparation of Arg (B31), Gly (A21) Human Insulin from a Fusion Protein which is Obtained by Yeast Secretion and Comprises the Proinsulin Correctly Folded, and whose Fusion Protein is Eliminated with the Enzyme Enterokinase DNA of the plasmid pADH2Hir_ins_glyA21 serves as starting material. The primer ins_gly_a21rev from example 7 of the present application and hirf1 from example 1 of the application WO 02/070722 A1 are used. For this purpose, two new primers are prepared:

Hir_entero_insf
5'-CTTCAG GACGATGACGATAAATTTGTTAACCAACACTTGTGTGG-3' (SEQ ID NO.: 11)

The primer covers the amino acids B1-B7 and B8 (partially) of the miniproinsulin sequence and comprises the codons for the amino acid sequence Asp-Asp-Asp-Asp-Lys, which represent recognition site for enterokinase.

Hir_entero_insrev
(SEQ ID NO.: 12)
5'-TTTATCGTCATCGTCCTGAAGGCTGAAGGTATTCCTCAGGG-3'

The reverse primer covers the amino acids 60-65 of the lepirudin sequence and comprises the codons for the amino acid sequence Asp-Asp-Asp-Asp-Lys (SEQ ID NO.:13), which represent recognition site for enterokinase. Firstly two PCR are carried out with the primer pairs hirf1/Hir_entero_insrev and Hir_entero_insf/ins_gly_a21_rev. The reaction products are isolated. Aliquots of the material are mixed and the mixture is employed in a third PCR as template for the primer pair hirf1/ins_gly_a21_rev. The reaction product is cloned as described. The result is the vector pADH2Hir_ins_glyA21. The fusion protein is prepared as described.

The fusion protein is cleaved with enterokinase. The enzyme is commercially available.

The cleavage reaction is carried out in enterokinase buffer (20 mM Tris/HCl, 50 mM NaCl, 2 mM CaCl$_2$ pH 7.4) employing an amount of enzyme corresponding to the particular manufacturer's information. The cleavage ordinarily takes place after removal of the host cells and the following workup step. However, it can also take place directly in the supernatant after fermentation, after the optimal reaction conditions have been adjusted.

EXAMPLE 13

Preparation of Arg (B31), Gly (A21) Human Insulin from a Fusion Protein which has been Obtained by Yeast Secretion and Comprises Proinsulin Correctly Folded, and Whose Fusion Portion is Eliminated with the Enzyme Enterokinase and Comprises a Polyhistidine Sequence DNA of the plasmid pADH2_LT_H6_Hir_ins_glyA21 and the primers Hir_entero_insrev, Hir_entero_insf and ins_gly_a21_rev are used, and primer hirf1 is replaced by the primer alpha_lt_enterof with the following sequence:

```
5'-GAAGGGGTACCTTTGGATAAAAG-3'    (SEQ ID NO.: 13)
```

Then, in analogy to example 12, a vector pADH2_LT_H6_Hir_etero_ins_glyA21 which codes for a fusion protein whose hirudin fusion portion has been extended by six histidines starting with position 3 N-terminally and C-terminally from position 72 by the sequence DDDDK (SEQ ID NO.: 14) is constructed.

Arg(B31), Gly(A21) human insulin is then prepared by combining the method described in examples 11 and 12.

EXAMPLE 14

Gene Sequence for Secretion of a Hirudin des-Phe (B1), Arg(B31), Gly(A21) Insulin Fusion Protein by Baker's Yeast The transformation and expression takes place in analogy to example 7.

Two primer sequences are synthesized:
Desphef1:

```
                                   (SEQ ID NO.: 15)
5'-CTTCAGGGAAATTCGGCACGAGTTAACCAACACTTGTGTGGTTC-3'
``` and Desphe_rev1:

```
                                   (SEQ ID NO.: 16)
5'-GAACCACACA AGTGTTGGTT AACTCGTGCC GAATTCCCT

GAAG-3'
```

DNA of the plasmid pADH2Hir_ins_glyA21 from example 7 serves as template. Two polymerase chain reactions are carried out independently of one another. In reaction 1, the primers Desphe_rev1 and the primer SEQ ID NO:4 from example 1 of the application EP-A 1 364 032 are employed, and in reaction 2 the primer ins_gly_a21rev from example 7 of the present application and the primer Desphef1 are employed. The reaction products of the two reactions are isolated and aliquots of the yield are combined in a third reaction and employed as template for the primer pair consisting of the primers SEQ ID NO:4 from example 1 of the application EP-A 1 364 032 and ins_gly_a21_rev. The reaction product of the third reaction is cloned, transformed and expressed as described in example 7. The resulting fusion protein serves as starting material for preparing corresponding insulin analogs with dibasic chain ends.

EXAMPLE 15

Gene Sequence for Secretion of a Hirudin Ala (B31), Arg(B32), Gly(A21) Insulin Fusion Protein by Baker's Yeast Two primer sequences are synthesized:
Ala_b31f1:

```
5'-CTTCTACACTCCAAAGACGgctCGTGGTATCGTTGAACAATGTTG-3'    (SEQ ID NO.: 17)
``` and Ala_b31 rev1:

```
                                   (SEQ ID NO.: 18)
5'-CAACATTGTT CAACGATACC ACGagcCGTC TTTGGAGTGT

AGAAG-3'
```

DNA of the plasmid pADH2Hir_ins_glyA21 from example 7 serves as template. Two polymerase chain reactions are carried out independently of one another. In reaction 1, the primers Ala_b31 rev1 and the primer SEQ ID NO:4 from example 1 of the application EP-A 1 364 032 are employed, and in reaction 2 the primer ins_gly_a21rev from example 7 of the present application and the primer Ala_b31f1 are employed. The reaction products of the two reactions are isolated and aliquots of the yield are combined in a third reaction and employed as template for the primer pair consisting of the primers SEQ ID NO:4 from example 1 of the application EP-A 1 364 032 and ins_gly_a21_rev. The reaction product of the third reaction is cloned, transformed and expressed as described in example 7. The resulting fusion protein serves as starting material for preparing corresponding insulin analogs with dibasic chain ends.

EXAMPLE 16

Gene Sequence for Direct Secretion of a Lys(B31) Precursor by Baker's Yeast

Two primers are synthesized:
Lys_b31f

```
                                   (SEQ ID NO.: 19)
5'-CTTCTACACTCCAAAGACGAAAGGTATCGTTGAACAATGTTG-3'
``` and Lys_b31rev

```
                                   (SEQ ID NO.: 20)
5'-CAACATTGTT CAACGATACC TTTCGTCTTT GGAGTGTAGA

AG-3'
```

DNA of the plasmid pADH2Hir_ins from example 1 of the application WO 02/070722A1 serves as template for two polymerase chain reactions. In reaction 1, the primers Lys_b31f1 and insnco1rev (Seq ID NO:6 from WO 02/070722A1) are employed, and in reaction 2 the primers Lys_b31 rev and alpha_insf1 from example 7 of the present application are employed. The standard reactions are carried out and the resulting PCR fragments are isolated. Aliquots of the two yields are combined and serve as template for a third reaction with the primers insncol rev and Seq ID NO:6 from WO 02/070722A1. The resulting PCR fragment is cloned and expressed as described in example 8. The result is Lys(B31)-miniproinsulin, which is converted with lysyl endopeptidase into B(1-29)-A(1-21) split insulin and as intermediate for preparing B30-argininamide insulin or B30 lysysinamide-insulin, which can subsequently be converted into the respective dibasic analog.

EXAMPLE 17

Cleavage with Lysyl Endopeptidase

The insulin precursor is reacted as described in DE3844211 with lysyl endopeptidase (LEP) (example 1). For this purpose, 10 mg of Lys(B31)-miniproinsulin are dissolved in Tris buffer (pH 8.0), and LEP from Lysobacter enzymogenes is added (0.01 ml of a 1 mg/ml conc. solution in water, Merckbiosciences). Incubation is carried out at room temperature for 2 h and purification is by RP-HPLC (Nucleosil 120-5 column). The result is B(1-29)-A(1-21) split insulin.

EXAMPLE 18

Preparation of Arg(B30)-insulin from a B(1-29)-A(1-21) Split Insulin Precursor by Coupling with Argininamide 100 mg of B(1-29)-A(1-21) split insulin are dissolved in 0.95 ml of argininamide solution (446 g/L), and 0.13 ml of M Na acetate buffer (pH 5.8) and 2 ml of DMF are added. The reaction mixture is cooled to 12° C. and started by adding 0.094 ml of trypsin (0.075 mg, Roche Diagnostics).

After 8 h, the reaction is stopped by adding TFA to pH 2.5 and analyzed by HPLC. >60%-Arg(B30)-insulinamide is formed. Addition of trypsin inhibitor solution is followed by purification of the amidated analog in analogy to U.S. Pat. No. 5,656,722. The amidated insulin analog can then be hydrolyzed in the presence of acid for several hours to give Arg (B30) insulin, or the amide can be employed directly as medicament.

EXAMPLE 19

Preparation of Lys(B30)-Insulin from a B(1-29)-A(1-21) Split Insulin Precursor by Coupling with Lysinamide 100 mg of B(1-29)-A(1-21) split insulin are dissolved in 0.93 ml of lysinamide solution (400 g/L), and 0.13 mL of M Na acetate buffer (pH 5.8) and 2 ml of DMF are added. The reaction mixture is cooled to 12° C. and started by adding 0.094 ml of trypsin (0.075 mg, Roche Diagnostics). After 8 h, the reaction is stopped by adding TFA to pH 2.5 and analyzed by HPLC. Lys(B30)-insulinamide is formed and is purified after addition of trypsin inhibitor solution in analogy to U.S. Pat. No. 5,656,722. The amidated insulin analog can then be hydrolyzed in the presence of acid for several hours to give Lys(B30)-insulin, or be employed directly as medicament.

---

What is claimed is:

1. A method for preparing a functional insulin analog or a derivative thereof, wherein the insulin analog is characterized by the general formula I:

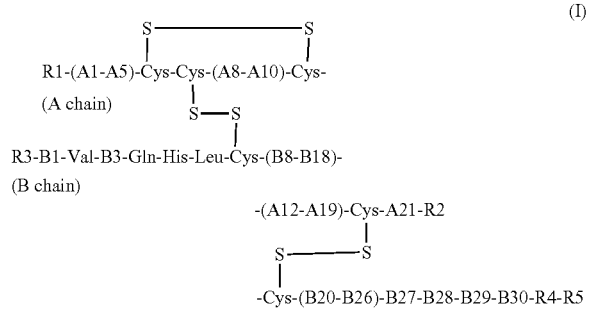

(I)

wherein
(A1-A5) are the amino acid residues in positions A1 to A5 of the A chain of human insulin or animal insulin,
(A12-A19) are the amino acid residues in positions A12 to A19 of the A chain of human insulin or animal insulin,
A21 is a naturally occurring amino acid residue,
(B8-B18) are the amino acid residues in positions B8 to B18 of the B chain of human insulin or animal insulin,
(B20-B26) are the amino acid residues in positions B20 to B26 of the B chain of human insulin or animal insulin,
(A8-A10) are the amino acid residues in positions A8 to A10 of the A chain of human insulin or animal insulin,
B30 is a chemical bond or a naturally occurring amino acid residue,
B1 is a chemical bond or a naturally occurring amino acid residue,
B3 is a naturally occurring amino acid residue,
each of B27, B28 and B29 is a naturally occurring amino acid residue,
R1 is an amino group or one to three naturally occurring amino acid residues,
R2 is a carboxy group or one to three naturally occurring amino acid residues,
R3 is an amino group or one to three naturally occurring amino acid residues,
R4 is a basic amino acid selected from the group consisting of Arg and Lys, and
R5 is one or two basic amino acid residues whose C terminus is either free or amidated,
said method comprising:
adding a naturally occurring, basic amino acid which is amidated or protected C-terminally with a protective group, onto an initial insulin analog or a derivative thereof whose C-terminal amino acid of the A and/or B chain is selected from a group comprising naturally occurring, basic amino acids or analogs or derivatives thereof, onto one of said C-terminal amino acids in the presence of an enzyme having the biological activity of trypsin in the presence of an organic solvent under conditions such that said enzyme catalyzes ligation to add said basic amino acid onto one of said C-terminal amino acids;
purifying the resulting modified insulin analog, and optionally
cleaving the amide group or C-terminal protective group of the added amino acid or of the added peptide.

2. The method as claimed in claim 1, wherein the initial insulin analog is characterized by the general formula II:

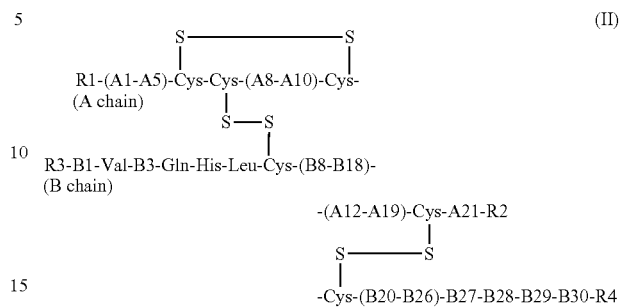

(II)

wherein R1, (A1-A5), (A8-A10), (A12-A19), A21, R2, R3, B1, B3, (B8-B18), (B20-B26), B27, B28, B29, B30 and R4 are defined as in claim 2, and the C-terminal amino acid residue of the B chain is selected from a group comprising naturally occurring, basic amino acids.

3. The method as claimed in claim 1, wherein the naturally occurring, basic amino acid which is amidated or protected C-terminally with a protective group is C-terminally amidated arginine or arginine protected C-terminally with a protective group.

4. The method as claimed in claim 2, wherein the naturally occurring, basic amino acid which is amidated or protected C-terminally with a protective group is C-terminally amidated arginine or arginine protected C-terminally with a protective group.

5. The method as claimed in claim 1, wherein the modified insulin analog is Gly(A21), Arg(B31), Arg(B32) human insulin whose C-terminal end of the B chain is amidated.

6. The method as claimed in claim 2, wherein the modified insulin analog is Gly(A21), Arg(B31), Arg(B32) human insulin whose C-terminal end of the B chain is amidated.

7. The method as claimed in claim 1, in which the initial insulin analog is Gly(A21), Arg(B31) human insulin.

8. The method as claimed in claim 1, wherein the initial insulin analog is prepared by recombinant expression of a precursor protein comprising the A chain and the B chain of the initial insulin analog.

9. The method as claimed in claim 8, wherein a gene which is part of a replicon is expressed.

10. The method as claimed in claim 8, wherein a bacterium or a yeast is used as host cell.

11. The method as claimed in claim 9, wherein a bacterium or a yeast is used as host cell.

12. The method as claimed in claim 8, wherein the precursor protein is secreted after expression.

13. The method as claimed in claim 12, wherein the precursor protein is isolated from the cellular supernatant of bacteria or yeasts.

14. The method for preparing modified insulin analogs as claimed in claim 10, wherein the precursor protein is isolated from the periplasm of a bacterium.

15. The method for preparing modified insulin analogs as claimed in claim 11, wherein the precursor protein is isolated from the periplasm of a bacterium.

16. The method as claimed in 8, wherein the precursor protein is subjected to a folding process and an enzymatic cleavage.

17. The method as claimed in claim 1, wherein the initial insulin analog is prepared by recombinant direct expression.

18. The method as claimed in claim 1, wherein the enzyme having the biological activity of trypsin is selected from a group consisting of human trypsin, porcine trypsin, bovine trypsin and a variant of human trypsin, porcine trypsin and bovine trypsin.

19. The method as claimed in claim 1, wherein the enzyme is having a lysyl endopeptidase activity.

20. The method as claimed in claim 1, wherein the C-terminal end of the B chain of the modified insulin analog is subsequently deprotected in a hydrolysis reaction.

21. The method as claimed in claim 1, in which the resulting insulin analog is Gly(A21), Arg(B31), Arg(B32) human insulin.

* * * * *

SEQUENCE LISTING

```
<160> NUMBER OF SEQ ID NOS: 20

<210> SEQ ID NO 1
<211> LENGTH: 97
<212> TYPE: PRT
<213> ORGANISM: Artificial
<220> FEATURE:
<223> OTHER INFORMATION: insulin fusion protein

<400> SEQUENCE: 1

Met Ala Thr Thr Ser Thr Gly Asn Ser Ala Arg Phe Val Asn Gln His
1               5                   10                  15

Leu Cys Gly Ser His Leu Val Glu Ala Leu Tyr Leu Val Cys Gly Glu
            20                  25                  30

Arg Gly Phe Phe Tyr Thr Pro Lys Thr Arg Arg Glu Ala Glu Asp Pro
        35                  40                  45

Gln Val Gly Gln Val Glu Leu Gly Gly Pro Gly Ala Gly Ser Leu
    50                  55                  60

Gln Pro Leu Ala Leu Glu Gly Ser Leu Gln Lys Arg Gly Ile Val Glu
65                  70                  75                  80

Gln Cys Cys Thr Ser Ile Cys Ser Leu Tyr Gln Leu Glu Asn Tyr Cys
                85                  90                  95

Gly

<210> SEQ ID NO 2
<211> LENGTH: 45
<212> TYPE: DNA
<213> ORGANISM: Artificial
<220> FEATURE:
```

-continued

<223> OTHER INFORMATION: Primer insu_a21_gly_rev

<400> SEQUENCE: 2 tttttttaagc ttgtcgactc attagccgca gtagttctcc agctg        45

<210> SEQ ID NO 3
<211> LENGTH: 45
<212> TYPE: DNA
<213> ORGANISM: Artificial
<220> FEATURE:
<223> OTHER INFORMATION: Primer ins_gly_a21_rev

<400> SEQUENCE: 3 tttttttccat gggtcgacta tcagccacag tagttttcca gctgg        45

<210> SEQ ID NO 4
<211> LENGTH: 48
<212> TYPE: DNA
<213> ORGANISM: Artificial
<220> FEATURE:
<223> OTHER INFORMATION: Primer alpha_insf1

<400> SEQUENCE: 4 tttttttggat cctttggaat aaaagatttg ttaaccaaca cttgtgtg        48

<210> SEQ ID NO 5
<211> LENGTH: 44
<212> TYPE: DNA
<213> ORGANISM: Artificial
<220> FEATURE:
<223> OTHER INFORMATION: Primer ins_gly_rev2

<400> SEQUENCE: 5 tttttttccat gggtcgctat cagccacagt agttttccag ctgg         44

<210> SEQ ID NO 6
<211> LENGTH: 49
<212> TYPE: DNA
<213> ORGANISM: Artificial
<220> FEATURE:
<223> OTHER INFORMATION: Primer ins_gly_rev2

<400> SEQUENCE: 6
tttttggcgc cgaattcact actattagcc acagtagttt tccagctgg     49

<210> SEQ ID NO 7
<211> LENGTH: 40
<212> TYPE: DNA
<213> ORGANISM: Artificial
<220> FEATURE:
<223> OTHER INFORMATION: Primer pich_insgly_dirf

<400> SEQUENCE: 7 tttttttctcg agaaaagatt tgttaaccaa cacttgtgtg              40

<210> SEQ ID NO 8
<211> LENGTH: 33
<212> TYPE: DNA
<213> ORGANISM: Artificial
<220> FEATURE:
<223> OTHER INFORMATION: Primer pich_insgly_dirrev

<400> SEQUENCE: 8 tttttttggcg ccgaattcac tactattagc cac                    33

<210> SEQ ID NO 9

```
<211> LENGTH: 39
<212> TYPE: DNA
<213> ORGANISM: Artificial
<220> FEATURE:
<223> OTHER INFORMATION: Primer alpha_LT_H6_hirf1

<400> SEQUENCE: 9
gcaccatcat caccatcact atactgactg cactgaatc                              39

<210> SEQ ID NO 10
<211> LENGTH: 48
<212> TYPE: DNA
<213> ORGANISM: Artificial
<220> FEATURE:
<223> OTHER INFORMATION: Primer alpha_LT_H6_hirf2

<400> SEQUENCE: 10 gaagggtac ctttggataa aagacttacg caccatcatc accatcac                     48

<210> SEQ ID NO 11
<211> LENGTH: 44
<212> TYPE: DNA
<213> ORGANISM: Artificial
<220> FEATURE:
<223> OTHER INFORMATION: Primer Hir_entero_insf

<400> SEQUENCE: 11
cttcaggacg atgacgataa atttgttaac caacacttgt gtgg                        44

<210> SEQ ID NO 12
<211> LENGTH: 41
<212> TYPE: DNA
<213> ORGANISM: Artificial
<220> FEATURE:
<223> OTHER INFORMATION: Primer Hir_entero_insrev

<400> SEQUENCE: 12
tttatcgtca tcgtcctgaa ggctgaaggt attcctcagg g                           41

<210> SEQ ID NO 13
<211> LENGTH: 23
<212> TYPE: DNA
<213> ORGANISM: Artificial
<220> FEATURE:
<223> OTHER INFORMATION: Primer alpha_lt_enterof

<400> SEQUENCE: 13 gaagggtac ctttggataa aag                                                23

<210> SEQ ID NO 14
<211> LENGTH: 5
<212> TYPE: PRT
<213> ORGANISM: Artificial
<220> FEATURE:
<223> OTHER INFORMATION: recognition sequence

<400> SEQUENCE: 14

Asp Asp Asp Asp Lys
1               5
```

```
<210> SEQ ID NO 15
<211> LENGTH: 44
<212> TYPE: DNA
<213> ORGANISM: Artificial
<220> FEATURE:
<223> OTHER INFORMATION: Primer Desphef1

<400> SEQUENCE: 15
cttcagggaa attcggcacg agttaaccaa cacttgtgtg gttc            44

<210> SEQ ID NO 16
<211> LENGTH: 44
<212> TYPE: DNA
<213> ORGANISM: Artificial
<220> FEATURE:
<223> OTHER INFORMATION: Primer Desphe_rev1

<400> SEQUENCE: 16
gaaccacaca agtgttggtt aactcgtgcc gaatttccct gaag            44

<210> SEQ ID NO 17
<211> LENGTH: 45
<212> TYPE: DNA
<213> ORGANISM: Artificial
<220> FEATURE:
<223> OTHER INFORMATION: Primer Ala_b31f1

<400> SEQUENCE: 17
cttctacact ccaaagacgg ctcgtggtat cgttgaacaa tgttg           45

<210> SEQ ID NO 18
<211> LENGTH: 45
<212> TYPE: DNA
<213> ORGANISM: Artificial
<220> FEATURE:
<223> OTHER INFORMATION: Primer Ala_b31rev1

<400> SEQUENCE: 18
caacattgtt caacgatacc acgagccgtc tttggagtgt agaag           45

<210> SEQ ID NO 19
<211> LENGTH: 42
<212> TYPE: DNA
<213> ORGANISM: Artificial
<220> FEATURE:
<223> OTHER INFORMATION: Primer Lys_b31f

<400> SEQUENCE: 19
cttctacact ccaaagacga aggtatcgt tgaacaatgt tg              42

<210> SEQ ID NO 20
<211> LENGTH: 42
<212> TYPE: DNA
<213> ORGANISM: Artificial
<220> FEATURE:
<223> OTHER INFORMATION: Primer Lys_b31rev

<400> SEQUENCE: 20
caacattgtt caacgatacc tttcgtcttt ggagtgtaga ag              42
```